US009909985B2

(12) United States Patent
Pacholski et al.

(10) Patent No.: US 9,909,985 B2
(45) Date of Patent: Mar. 6, 2018

(54) MULTIPLE SUPERIMPOSED INTERFACE PATTERN POROUS MICROSTRUCTURE MULTI LAYER BIOSENSING METHOD

(75) Inventors: Claudia Pacholski, Hamburg (DE); Gordon M. Miskelly, Avondale (NZ); Michael J. Sailor, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 2368 days.

(21) Appl. No.: 12/683,895

(22) Filed: Jan. 7, 2010

(65) Prior Publication Data
US 2011/0170106 A1  Jul. 14, 2011

Related U.S. Application Data

(62) Division of application No. 11/371,319, filed on Mar. 8, 2006, now abandoned.

(60) Provisional application No. 60/660,421, filed on Mar. 10, 2005.

(51) Int. Cl.
*G01J 3/45* (2006.01)
*G01N 21/55* (2014.01)
*G01J 3/26* (2006.01)

(52) U.S. Cl.
CPC ............... *G01N 21/55* (2013.01); *G01J 3/26* (2013.01)

(58) Field of Classification Search
CPC .................................. G01N 21/55; G01J 3/26
See application file for complete search history.

(56) References Cited

U.S. PATENT DOCUMENTS

| | | | |
|---|---|---|---|
| RE33,581 E | 4/1991 | Nicoli et al. | |
| 5,071,248 A | 12/1991 | Tiefenthaler et al. | |
| 5,218,472 A | 6/1993 | Jozefowicz et al. | |
| 5,318,676 A | 6/1994 | Sailor et al. | |
| 5,468,606 A | 11/1995 | Bogart et al. | |
| 5,763,176 A | 6/1998 | Stater et al. | |
| 5,928,726 A | 7/1999 | Butler et al. | |
| 6,248,539 B1 | 6/2001 | Ghardi et al. | |
| 6,355,431 B1 | 3/2002 | Chee et al. | |
| 6,396,995 B1 | 5/2002 | Stuelpnagel et al. | |
| 6,429,027 B1 | 8/2002 | Chee et al. | |
| 6,544,732 B1 | 4/2003 | Chee et al. | |
| 6,620,584 B1 | 9/2003 | Chee et al. | |
| 6,630,356 B1 | 10/2003 | Armstrong et al. | |
| 6,645,045 B2 * | 11/2003 | Ohkawa | 451/6 |
| 6,663,832 B2 | 12/2003 | Lebl et al. | |
| 6,720,177 B2 | 4/2004 | Ghadiri et al. | |
| 6,770,441 B2 | 8/2004 | Dickinson et al. | |
| 6,812,005 B2 | 11/2004 | Fan et al. | |
| 6,846,460 B1 | 1/2005 | Lebl | |
| 6,858,394 B1 | 2/2005 | Chee et al. | |
| 7,226,733 B2 | 6/2007 | Chan et al. | |
| 2002/0192680 A1 | 12/2002 | Chan et al. | |
| 2003/0146109 A1 | 8/2003 | Sailor et al. | |
| 2004/0244889 A1 | 12/2004 | Sailor et al. | |
| 2005/0009374 A1 | 1/2005 | Gao et al. | |
| 2005/0042764 A1 | 2/2005 | Sailor et al. | |
| 2006/0051872 A1 | 3/2006 | Sailor et al. | |

OTHER PUBLICATIONS

Anglin et al, Engineering the chemistry and nanostructure of porous silicon Fabry-Perot films for loading and release of a steroid, Langmuir, 2004, vol. 20, p. 11264-11269.*
Allcock et al., Time-resolved sensing of organic vapors in low modulating porous silicon dielectric mirrors, Journal of Applied Physics, vol. 90, 2001, p. 5052-5057.*
SNow et al., Vapor sensing using the optical properties of porous silicon Bragg mirrors, Journal of Applied Physics, vol. 86, 1999, p. 1781-1784.*
Striemer, C.C., et. al., "Charge-and size-based separation of macromolecules using ultrathin silicon membranes", *Nature*, 445 (7129), 749 (2007).
Jones, L. J. et al., "Quenched BODIPY dye-labeled casein substrates for the assay of protease activity by direct fluorescence measurement", *Anal. Biochem.* 251 (2), 144 (1997).
Schwartz, Michael P., et. al., "A porous SiO2 Interferometric Biosensor for quantitative determination of protein interactions: binding of protein A to immunoglobulins derived from different species", *Anal. Chem.* 79, 327 (2007).
Park, J. S. et al., "Enhancement of sensitivity in interferometric biosensing by using a new biolinker and prebinding antibody", *J. Microbiol. Biotechnol.* 16 (12), 1968 (2006).
Wiesner, R., et. al. "A new assay for proteases using fluorescent labeling of proteins", *Anal. Biochem.* 121 (2), 290 (1982).
Tinsley-Bown, A. et al., "Immunoassays in a porous silicon interferometric biosensor combined with sensitive signal processing", *Phys. Status Solidi A—Appl. Mat.* 202 (8), 1347 (2005).
Lin, V. S.-Y. et al., "A porous silicon-based optical interferometric Biosensor", *Science* 278 (5339), 840 (1997).
Pacholski, Claudia et al., "Reflective interferometric Fourier transform spectroscopy: a self-compensating label-free immunosensor using doublelayers of porous SiO2", *J. Am. Chem. Soc.* 128, 4250 (2006).

(Continued)

*Primary Examiner* — Taeyoon Kim
*Assistant Examiner* — Tiffany Gough
(74) *Attorney, Agent, or Firm* — Greer, Burns & Crain, Ltd.; Steven P. Fallon

(57) ABSTRACT

A preferred embodiment biosensor is a multi-layer microporous thin film structure. Pores in a top layer of the micro-porous thin film structure are sized to accept a first molecule of interest. Pores in a second layer of the microporous thin film structure are smaller than the pores in the top layer and are sized to accept a second molecule of interest that is smaller than the first molecule of interest. The pores in the second layer are too small to accept the first molecule of interest. The pores in the top layer and the pores in the second layer are sized and arranged such that light reflected from the multi-layer micro-porous thin film structure produces multiple superimposed interference patterns that can be resolved. In preferred embodiments, the multi-layer micro-porous thin film structure is a porous silicon thin film multi-layer structure formed on a silicon substrate, such as a silicon wafer. Specific and nonspecific binding can be detected with biosensors of the invention. The position of peaks in the Fourier transform of the reflection spectrum and the shift in peak amplitudes can be used to determine the presence and quantity of targeted biological molecules of interest.

5 Claims, 7 Drawing Sheets

(56) References Cited

OTHER PUBLICATIONS

Pacholski, Claudia et al., "Biosensing using porous silicon double-layer interferometers: reflective interferometric Fourier transform spectroscopy", *J. Am. Chem. Soc.* 127 (33), 11636 (2005).

Kilian, Kristopher A. et al., "Peptide-modified optical filters for detecting protease activity" *ACS Nano* 1 (4), 355 (2007).

Orosco, Manuel M., et. al., "Protein-coated porous silicon photonic crystals for amplified optical detection of protease activity", *Adv. Mater.* 18, 1393 (2006).

Zhang, X. G., "Porous Silicon: Morphology and Formation Mechanisms", *J. Electrochem. Soc.* 151 (1), C69 (2004).

Leong, W. Y., et. al., "Electrically enhanced erosion of porous Si material in electrolyte by pH modulation and its application in chronotherapy", *Phys. Status Solidi A—Appl. Mat.* 204 (5), 1486 (2007).

Thomas, J. Christopher, et. al., "Delivery of nanogram payloads using magnetic porous silicon Microcarriers", *Lab Chip* 6 (6), 782 (2006).

Collins, Boyce E., et. al., "Determining protein size using an electrochemically machined pore gradient in silicon", *Adv. Funct. Mater.* 12 (3), 187 (2002).

Schwartz, Michael P. et al., "The smart petri dish: A nanostructured photonic crystal for real-time monitoring of living cells", *Langmuir* 22, 7084 (2006).

Fruton, Joseph S., "The Active site of Pepsin", *Acc. Chem. Res.* 7 (8), 241 (1974).

Inouye, Ken et.al., "Inhibition of Pepsin Action", *Biochemistry* 7 (5), 1611 (1968).

Fujinaga, M. et al., "Crystal structure of human pepsin and its complex with Pepstatin", *Protein science : a publication of the Protein Society* 4 (5), 960 (1995).

Sachdev, Goverdhan P., et. al., "Kinetics of action of pepsin on fluorescent peptide substrates",*Proc. Nat. Acad. Sci.* 72 (9), 3424 (1975).

Eric J. Lee et al., "Photoderivation of the Surface of Luminescent Porous Silicon with Formic Acid", *J. Am. Chem. Soc.*, vol. 117, 8295-96 (1995).

V.S.Y. Lin et al., "A Porous Silicon-Based Optical Interferometric Biosensor", *Science*, vol. 278, pp. 840-842 (Oct. 31, 1997).

Andreas Janshoff et al., "Macroporous p-Type Siicon Fabry-Perot Layers. Fabrication, Characterization, and Applications in Biosensing", *J. Am. Chem. Soc.*, vol. 120, pp. 12108-12116 (1998).

S. R. Nicewarner-Peña et al., "Submicrometer Metallic Barcodes", *Science*, vol. 294, pp. 137-141 (Oct. 5, 2001).

L. Pavesi et al., "Random Porous Silicon Multilayers: Application to Distributed Bragg Reflectors and Interferential Fabry-Pérot Filters", *Semicond. Sci. Technol.*, vol. 12, pp. 570-575 (1997).

D. Van Noort et al., "Monitoring Specific Interaction of Low Molecular Weight Biomolecules on Oxidized Porous Silicon Using Ellipsometry", *Biosensors & Bioelectronics*, vol. 13, No. 3-4, pp. 439-449 (1998).

M. Thonissen et al., Section 1.4, "Multilayer Structures of Porous Silicon", In *Properties of Porous Silicon*, (Eds: L. Canham). EMIS Datareviews, vol. 8, Short Run Press Ltd., London, pp. 30-37 (1997).

Honglae Sohn et al., "Detection of Fluorophosphonate Chemical Warefare Agents by Catalytic Hydrolysis with a Porous Silicon Interferometer", *J. Am. Chem. Soc.*, vol. 122, pp. 5399-5400 (2000).

M.J. Sailor, "Sensor Applications of Porous Silicon", Section 12.4, In *Properties of Porous Silicon*, (Eds: L. Canham). EMIS Datareviews, vol. 8, Short Run Press Ltd., London, pp. 364-370 (1997).

J.R. Quagliano et al., "Quantitative Chemical Identification of Four Gases in Remote Infrared (9-11 μm) Differential Absorption Lidar Experiments", *Applied Optics*, vol. 36, No. 9, pp. 1915-1927 (Mar. 20, 1997).

M.J. Sailor et al., "Low-Power Microsenors for Explosives and Nerve Warfare Agents Using Silicon Nanodots and Nanowires", In SPIE Meeting on Unattended Ground Sensor Technologies and Applications, (Ed: E.M. Carapezza, D.B. Law and K.T. Stalker). SPIE, vol. 4393, pp. 153-165, 2000.

B. Warneke et al., "Smart Dust: Communicating with a Cubic-Millimeter Computer", *Computer*, pp. 44-51 (Jan. 2001).

V.G. Cheung et al., "Making and Reading Microarrays", *Nature Genetics Supplement*, vol. 21, pp. 15-19, (Jan. 1999).

L.T. Canham et al., "Derivatized Porous Silicon Mirrors: Implantable Optical Components with Slow Resorbability", *Physica*, vol. 182, No. 1, pp. 521-525 (2000).

A.P. Bowditch, "In-Vivo Assessment of Tissue Compatibility and Calcification of Bulk and Porous Silicon", *Materials Research Society Symp. Proc.*, vol. 536, pp. 149-154 (1999).

S. Chan et al., "Porous Silicon Microcavities for Biosensing Applications", *Phys. Stat. Sol.*, vol. 182, pp. 541-546 (2000).

"Abstracts of Oak Ridge Posters", *Clinical Chem.*, vol. 46, No. 9, pp. 1487-1522 (2000).

K.P.S. Dancil et al., "A Porous Silicon Optical Biosensor: Detection of Reversible Binding of IgG to a Protein A—Modified Surface," *J. Am. Chem. Soc.*, vol. 121, pp. 7925-7930 (1999).

J.H. Holtz et al., "Polymerized Colloidal Crystal Hydrogel Films as Intelligent Chemical Sensing Materials", *Nature*, vol. 389, pp. 829-832 (Oct. 23, 1997).

J. Gao et al., "Porous-Silicon Vapor Sensor Based on Laser Interferometry", *Applied Physics Letters*, vol. 77, No. 6, pp. 901-903 (Aug. 7, 2000).

J.M. Lauerhaas et al., "Chemical Modification of the Photoluminescence Quenching of Porous Silicon", *Science*, vol. 261, pp. 1567-1568 (Sep. 17, 1993).

J.L. Heinrich et al., "Luminescent Colloidal Silicon Suspension from Porous Silicon", *Science*, vol. 255, No. 5040, pp. 66-68 (Jan. 3, 1992).

M.D. Ray et al., "Ultraviolet Mini-Raman Lidar for Stand-Off, in situ, Identification of Chemical Surface Contaminants", *Review of Scientific Instruments*, vol. 71, No. 9, pp. 3485-3489 (Sep. 2000).

N.F. Starodub et al., "Use of the Silicon Crystals Photoluminescence to Control Immunocomplex Formation", *Sensors and Actuators*, pp. 44-47, (1996).

M.J. Sailor et al., "Detection of DNT, TNT, HF and Nerve Agents Using Photoluminescence and Interferometry from a Porous Silicon Chip", In *Unattended Ground Sensor Technologies and Applications II*, Proceedings of SPIE, vol. 4040, pp. 95-104 (2000).

L. Pavesi et al., "Controlled Photon Emission in Porous Silicon Microcavities", *Appl. Phys. Lett.*, vol. 67, No. 22, pp. 3280-3282 (Nov. 27, 1995).

C. Mazzoleni et al., "Application to Optical Components of Dielectric Porous Silicon Multilayers", *Appl. Phys. Lett.*, vol. 67, No. 20, pp. 2983-2985 (Nov. 13, 1995).

V. Lehmann et al., "Optical Shortpass Filters Based on Macroporous Silicon", *Applied Physics Letters*, vol. 78, No. 5, pp. 589-591 (Jan. 29, 2001).

A.M. Tinsley-Bown et al., "Tuning the Pore Size and Surface Chemistry of Porous Silicon for Immunoassays", *Phys. Stat. Sol.*, vol. 182, pp. 547-553 (2000).

P.A. Snow et al., "Vapor Sensing using the Optical Properties of Porous Silicon Bragg Mirrors", *Journal of Applied Physics*, vol. 86, No. 4, pp. 1781-1784 (Aug. 15, 1999).

G. Vincent, "Optical Properties of Porous Silicon Superlattices", *Appl. Phys. Lett.*, vol. 64, No. 18, pp. 2367-2369 (May 2, 1994).

V. Wulfmeyer et al., "Ground-Based Differential Absorption Lidar for Water-Vapor Profiling: Assessment of Accuracy, Resolution, and Meteorological Applications", *Applied Optics*, vol. 37, No. 18, pp. 3825-3844 (Jun. 20, 1998).

M. Bruchez, Jr. et al., "Semiconductor Nanocrystals as Fluorescent Biological Labels", *Science*, vol. 281, pp. 2013-2016 (Sep. 25, 1998).

C.B. Carlisle et al., "$CO_2$ Laser-Based Differential Absorption Lidar System for Range-Resolved and Long-Range Detection of Chemical Vapor Plumes", *Applied Optics*, vol. 34, No. 27, pp. 6187-6200 (Sep. 20, 1995).

S. Chan et al., "Identification of Gram Negative Bacteria Using Nanoscale Silicon Microcavities", *J. Am. Chem. Soc.*, vol. 123, No. 47, pp. 11797-11798 (2001).

(56) References Cited

OTHER PUBLICATIONS

C.L. Curtis et al., "Observation of Optical Cavity Modes in Photoluminescent Porous Silicon Films", *J. Electrochem. Soc.*, vol. 140, No. 12, pp. 3492-3494 (Dec. 1993).

S. Content et al., "Detection of Nitrobenzene, DNT, and TNT Vapors by Quenching of Porous Silicon Photoluminescence", *Chem. Eur. J.*, vol. 6, No. 12, pp. 2205-2213 (2000).

D. Gerion et al., "Synthesis and Properties of Biocompatible Water-Soluble Silica-Coated CdSe/ZnS Semiconductor Quantum Dots", *J. Phys. Chem. B*, vol. 105, pp. 8861-8871 (2001).

M.R. Henry, et al., "Real-Time Measurements of DNA Hybridization on Microparticles with Fluorescence Resonance Energy Transfer", *Analytical Biochemistry*, vol. 276, pp. 204-214 (1999).

P. Coronado et al., "New Technologies to Support NASA's Mission to Planet Earth Satellite Remote Sensing Product Validation: The Use of an Unmanned Autopiloted Vehicle (UAV) as a Platform to Conduct Remote Sensing", Part of the SPIE Conference on Robotic and Semi-Robotic Ground Vehicle Technology, Orlando, FL Apr. 1998, vol. 3366, pp. 38-49.

D.F. Shriver, "The Manipulation of Air-Sensitive Compounds", 2d Ed., John Wiley & Sons, Inc. New York, 1986, pp. 290-311.

F. Cunin et al., "Biomolecular Screening with Encoded Porous-Silicon Photonic Crystals", Nature Materials, vol. 1, pp. 39-41. (Sep. 2002).

M.G. Berger et al., "Dielectric Filters Made of Porous Silicon: Advanced Performance by Oxidation and New Layer Structures", Thin Solid Films, vol. 297, pp. 237-240 (1997).

H. Fenniri et al., J. Am. Chem. Soc., vol. 123, pp. 8151-8152 (2001).

H. Fenniri et al., Angew. Chem. Int. Ed., vol. 39, pp. 4483-4485 (2000).

W.C.W. Chan et al., "Quantum Dot Bioconjugates for Ultrasensitive Nonisotopic Detection", Science, vol. 281, pp. 2016-2018 (1998).

J.A. Ferguson et al., "A Fiber Optic DNA Biosensor Microarray for the Analysis of Gene Expression", Nature Biotechnol, vol. 14, pp. 1681-1684 (1996).

M. Thonissen et al., "Multilayer Structures of Porous Silicon," Properties of Porous Silicon, vol. 18, pp. 30-37, (ed. L. Canham) (Short Run, London 1997).

A. Halimaoui, "Porous Silicon Formation by Anodisation," Properties of Porous Silicon, vol. 18, pp. 12-22, (ed. L. Canham) (Short Run, London 1997).

Pacholski et al., "Biomolecule Size Discrimination Using Porous Silicon Double-Layers: Determination by Fourier Transform Reflectivity Spectroscopy," pp. 1-31.

Dancil, Keiki-Pua et. al., "A Porous Silicon Optical Biosensor Detection of Reversible Binding of IgG to a Protein A—Modified Surface", *J. Am. Chem. Soc.*, 1999, vol. 121 pp. 7925-7930.

Striemer, C.C., et. al., "Charge- and size-based separation of macromolecules using ultrathin silicon membranes", *Nature*, 445 (7129), 749 (2007).

Jones, L. J. et al, "Quenched BODIPY dye-labeled casein substrates for the assay of protease activity by direct fluorescence measurement", *Anal. Biochem.* 251 (2), 144 (1997).

Zhang, X. G., "Morphology and formation mechanisms of porous silicon", *J. Electrochem. Soc.* 151 (1), C69 (2004).

Fruton, Joseph S., "Active site of pepsin", *Acc. Chem. Res.* 7 (8), 241 (1974).

Fujinaga, M. et al., "Crystal structure of human pepsin and its complex with Pepstatin", *Protein science : a publication of the Protein Society* 4 (5), 960, (1995).

Zangooie, S. et. al., "Protein adsorption in thermally oxidized porous silicon layers", Thin Solid Films 313-314 (1998) 825-830.

* cited by examiner

MULTIPLE SUPERIMPOSED INTERFACE PATTERN POROUS MICROSTRUCTURE MULTI LAYER BIOSENSING METHOD

REFERENCE TO RELATED APPLICATION AND PRIORITY CLAIM

This application is a divisional application of and claims priority under 35 U.S.C. § 120 from prior application Ser. No. 11/371,319, entitled Porous Microstructure Multi Layer Spectroscopy and Biosensing, which was filed on Mar. 8, 2006; and under 35 U.S.C. § 119 to provisional application Ser. No. 60/660,421 filed on Mar. 10, 2005 and entitled Porous Microstructure Multi Layer Spectroscopy and Biosensing.

STATEMENT OF GOVERNMENT INTEREST

The invention was made with government support under N01-CO-37117 awarded by National Cancer Institute and with government support under F49620-02-1-0288 awarded by Air Force Office of Scientific Research. The Government has certain rights in the invention.

FIELD OF THE INVENTION

A field of the invention is biosensing. Particular example applications for porous microstructures of the invention include label-free biomolecule sensing.

BACKGROUND

Porous microstructures have been demonstrated to produce characteristic spectral interference patterns. Porous silicon has been used to produce characteristic spectral interference patterns, and other semiconductors and insulators can be etched to produce characteristic spectral interference patterns. Introduction of analyte into such a porous microstructure produces a shift in the spectral interference pattern. The interference based sensing is largely impervious to less complex optical sensing and detection methods.

As an example, chemical or biomolecule detection can be based on changes in the spectral interference pattern that results from the reflection of white light at the interfaces above (air or solution) and below a porous silicon layer formed in a silicon wafer. Spectral positions of the Fabry-Pérot fringes shift as a function of the refractive index of the material filling the pores. Biomolecule penetration into the pores of porous Si layers, driven either by nonspecific adsorption or by specific binding (to an antibody, for instance) is observed as a shift of the Fabry-Pérot fringes to longer wavelengths. This corresponds to an increase in refractive index of the film as protein displaces aqueous solution in the pores.

The tuning of pore sizes, patterns and distributions in layers, such as porous silicon has been demonstrated. Pores can be tuned to trap a particular analyte, for example based upon pore size or by preparing the pores with a material to bind analyte. Pore size is controlled by an appropriate choice of electrochemical etching conditions. A biosensor can be formed, for example, by tuning pore size to accommodate a biomolecule of interest while keeping the pores small enough to avoid light scattering effects. Etching conditions affect pore size. Conditions that can affect pore size include, for example, the type of material being etched, doping levels (if any), resistivity, etching current density, etc. A wide range of pore sizes and morphologies can be obtained.

Single layer porous microstructures that are based on changes in the spectral interference pattern have been used. Others have used multi-layer porous silicon to achieve biosensors based on optical transduction methods other than wavelength shifts of the interference pattern. For example, Martin-Palma et al. detected binding of polyclonal mouse antibodies to an amine-modified porous Si multilayer by observing a reduction of the intensity of reflected light. Martin-Palma, et al. Microelectronics Journal, 2004, Vol. 35, pp. 45-48. Additionally, Chan et al. formed porous Si multilayer structures such as Bragg mirrors and microcavity resonators and used modulation of the photoluminescence spectra from these structures to distinguish between Gram (−) and Gram(+) bacteria. Chan et al., Journal of the American Chemical Society, 2001, Vol. 123, pp. 11797-11798. The non-interference based sensing methods have difficulty in noisy environments, require more sensitive equipment to achieve comparable sensitivity, and fail to account for common measurement conditions, e.g., signal drift due to thermal fluctuation, changes in sample composition, or degradation of the sample matrix.

Porous silicon films with a distribution of pore diameters in the x-y plane (parallel to the surface of the wafer) have been demonstrated as size-exclusion matrices to perform an on-chip determination of macromolecule dimensions. Karlsson, et al, H. J. Colloid Interface Sci., 2003, 266, 40-47. These films were generated by electrochemically etching Si in aqueous ethanolic HE using an asymmetric electrode configuration. Biomolecules penetrate the film and are detected only in regions where the pores are large enough. A disadvantage of this approach is that determination of protein size requires optical sampling over a relatively large area of the porous Si film.

SUMMARY OF THE INVENTION

A preferred embodiment biosensor is a multi-layer microporous thin film structure. Pores in a top layer of the micro-porous thin film structure are sized to accept a first molecule of interest. Pores in a second layer of the micro-porous thin film structure are smaller than the pores in the top layer and are sized to accept a second molecule of interest that is smaller than the first molecule of interest. The pores in the second layer are too small to accept the first molecule of interest. The pores in the top layer and the pores in the second layer are sized and arranged such that light reflected from the multi-layer micro-porous thin film structure produces multiple superimposed interference patterns that can be resolved. In preferred embodiments, the multi-layer micro-porous thin film structure is a porous silicon thin film multi-layer structure formed on a silicon substrate, such as a silicon wafer. Specific and nonspecific binding can be detected with biosensors of the invention. A shift in the position of peaks in the Fourier transform of the reflection spectrum and/or a shift in the intensity of the peak amplitudes can be used to determine the presence and quantity of targeted biological molecules of interest.

DETAILED DESCRIPTION OF THE PREFERRED EMBODIMENTS

A preferred embodiment of the invention is a biosensor. A sensor of the invention include a multi-layer micro-porous thin film structure, where the layers have pores of different sizes. The pores are sized and arranged in the multi-layer structure to produce optical interference patterns. In a preferred biosensor, pores in a top layer of the micro-porous thin film structure are sized to accept a first molecule of interest. Pores in a second layer of the micro-porous thin film structure are smaller than the pores in the top layer and are sized to accept a second molecule of interest that is smaller than the first molecule of interest. Pores in the second layer are too small to accept the first molecule of interest. Pores in the top layer and said pores in said second layer are sized and arranged such that light reflected from the multi-layer micro-porous thin film structure produces multiple superimposed interference patterns that can be resolved.

An example embodiment biosensor demonstrates an optical interferometer that incorporates a reference channel into the optical response of the structure. In an example embodiment, the pore sizes in different layers also provide for separation and detection of the analyte of interest. In additional embodiments, the pores in separate layers are also biologically prepared, e.g. with at least one layer among layers having differently sized pores contains an antibody.

Figure 1:
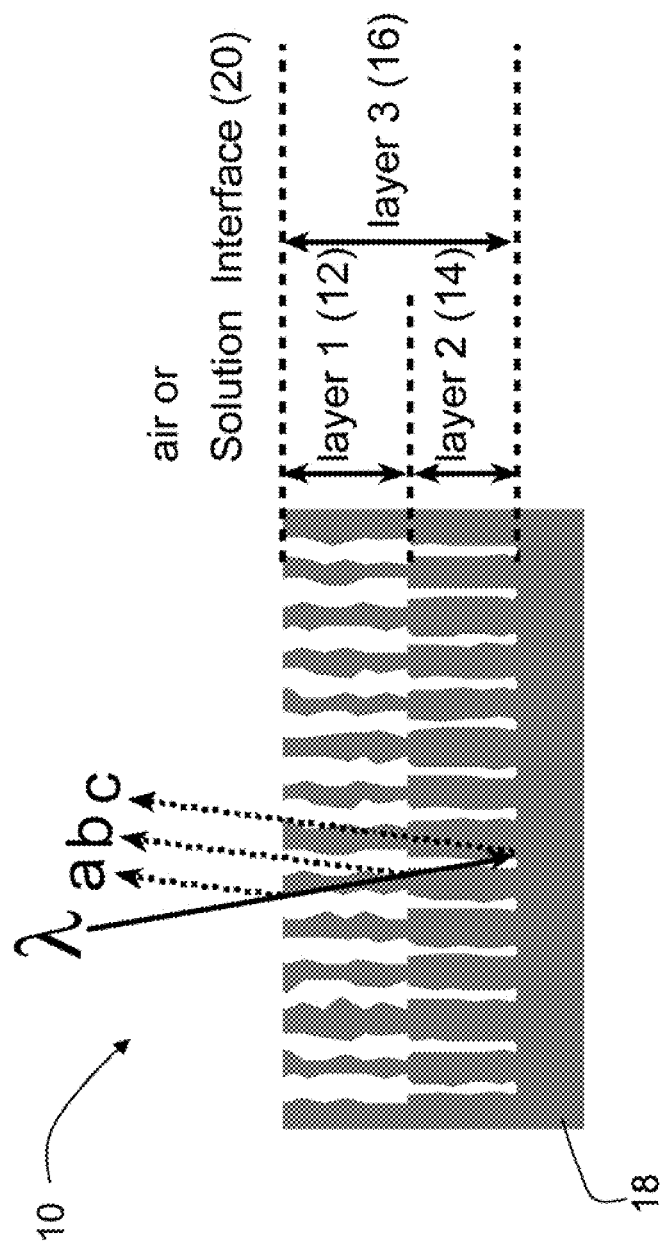
FIG. 1 is a schematic diagram of a preferred embodiment multi-layer biosensor of the invention.

Referring now to the drawings, a preferred biosensor 10 is shown in FIG. 1. The biosensor 10 is a thin film microstructure that includes layers 12 and 14, each of which has a porosity that produces an interference pattern in the Fourier transform of the optical reflectivity response. The combination of the layers 12 and 14 can be considered a third layer, as it produces an additional optical response. Pores in the layers 12 and 14 discriminate biomolecules based upon size. In a preferred embodiment, the porous layers 12 and 14 are porous silicon layers formed, e.g., in a silicon wafer 18. Other materials can be used, as well, such as other semiconductors or insulators.

Size discrimination occurs in the z direction (perpendicular to the plane of the wafer surface, at an air or solution interface). The layer 12 includes pores sized to accept a first molecule of interest. Pores in the second layer 14 of the micro-porous thin film structure are smaller than pores in the top layer 12 and are sized to accept a second molecule of interest that is smaller than the first molecule of interest. Light λ reflected from the layers 12, 14, 16 contains three superimposed interference patterns a, b, and c, which can be resolved by fast Fourier transform (FFT) of the reflectivity spectrum. Interference of beams a and b occurs from reflections at the interfaces bordering layer 1, interference of beams b and c originates from layer 2, and interference of beams a and c originates from layer 3. Analyte-containing solution is introduced at the top of the structure. The three peaks in the FFT provide an indication of the relative partitioning of the large and small molecules in the two layers of this size-selective membrane. Additional layers would produce additional superimposed interference patterns.

The ability of the pores in the layers 12 and 14 to discriminate among biomolecules of interest has been verified experimentally. Experiments were conducted with bovine serum albumin (BSA) and sucrose as the large and small probe molecules, respectively. Penetration of BSA exclusively into the top (large pore) layer and of sucrose into both layers is detected by optically allowing the detection of the larger BSA in the presence of a 100-fold (by mass) excess of sucrose. Artisans will recognize that the general applicability to other biomolecules, as well, and will appreciate additional details of preferred embodiments as well as broader aspects of the invention from the following experimental results. The work here demonstrates a simple and powerful means to discriminate and detect molecules based on size and to correct for drift in composition and other matrix effects with a designed nanostructure.

BSA and Sucrose

Sensing Experimental Results

1. Fabrication and Stabilization of p-Type Porous Si Double-Layers

Porous silicon (Si) double-layers with a layer of larger pores on top of a layer with smaller pores can be prepared using an electrochemical etch consisting of a short period of high applied current followed by a longer period at low current. In the experiments, the current density profile consisted of 11 s at 500 mA/cm$^2$ followed by 55 s at 167 mA/cm$^2$. This waveform was applied to a highly doped ($10^{-3}$ Ω-cm) p-type (100)-oriented single crystal Si wafer in ethanolic HF solution. For comparison, individual single-layer structures were also prepared. "Single-layer 1" was prepared using the first part of the double-layer waveform (11 s at 500 mA/cm$^2$), and "single-layer 2" was prepared using the second part of the double-layer waveform (55 s at 167 mA/cm$^2$). The resulting freshly etched porous Si samples are hydride-terminated and slowly degrade in air or water by oxidative or hydrolytic corrosion. To prevent corrosion in the aqueous solutions used in experiments, siloxy-terminated porous Si surfaces were prepared by thermal oxidation. Oxidation increases the hydrophilicity of porous Si, allowing water to effectively infiltrate the pores.

2. Determination of Porosity and Thickness of Porous Si Layers

The porosities and thicknesses of the individual porous Si layers were independently determined by gravimetry, SEM (thickness only) and by optical measurements. The average values obtained from at least three measurements are summarized in Table 1. Gravimetric measurements were performed by weighing the sample before etch, after etch, and after chemical dissolution of the porous layer. Cross-sectional scanning electron microscopy (SEM) reveals that the conditions used to prepare "single-layer 1" (11 s at 500 mA/cm$^2$) produce a ~2600 nm-thick porous Si film with cylindrical pores possessing diameters of ~50 to 100 nm. The conditions used to prepare "single-layer 2" (55 s at 167 mA/cm$^2$) produce a film of ~5400 nm in thickness. The pores in this layer are smaller, with diameters that are too small to be reliably resolved in the SEM images (<20 nm).

The results are confirmed by an approximately exponential dependence of the pore diameter on the current density for highly-doped p-type samples, a fact that has been previously recognized. The porous Si double-layer, produced by applying the "single-layer 1" etching conditions followed immediately by the "single-layer 2" conditions, possesses a combination of the two single layers one on top of the other. An SEM image obtained of the sample displayed the porous structure; layer thicknesses (~2900 nm and ~5600 nm for layers 1 and 2, respectively), and pore sizes were consistent with the images obtained from the single-layers.

when the porous Si film is oxidized. The gravimetry instead measures of the amount of Si lost in etching. Thus, in the case of oxidized porous Si films, gravimetry provides an under-estimation of film thickness. The SEM and optical measurements are more accurate measures of film thickness.

3. Interpretation of Interferometric Reflectance Spectra

Figure 2:
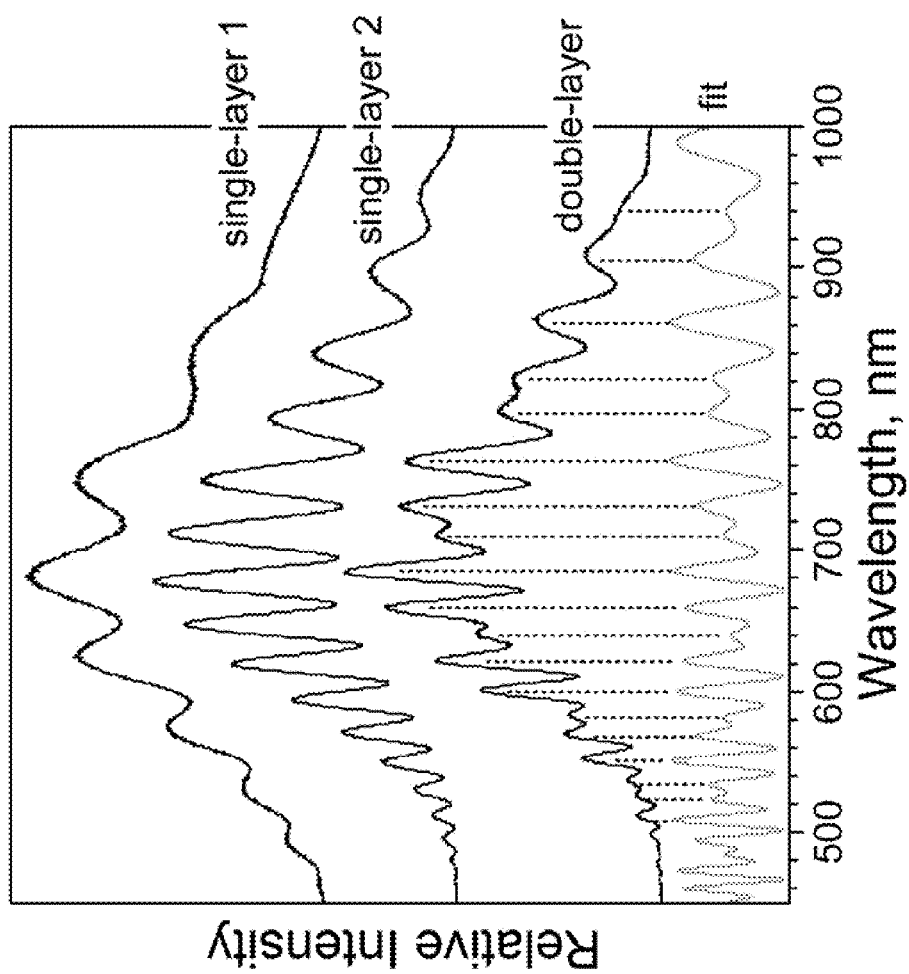
FIG. 2 shows reflectivity spectra of thermally oxidized porous Si single- and double-layers, the double layer structure representing an example experimental embodiment consistent with FIG. 1.

FIG. 2 displays reflectivity spectra of thermally oxidized porous Si single- and double-layers. FIG. 2 shows relative reflectance spectra of thermally oxidized porous Si single- and double-layers. "single-layer 1" is the spectrum of a single layer etched for 11 s at 500 mA/cm$^2$. "single-layer 2" corresponds to the single layer etched for 55 s at 167 mA/cm$^2$. "double-layer" corresponds to the double-layer

TABLE 1

Porosity and Thickness of Thermally Oxidized Porous Si Layers[a]

| Porous Si Layer | Gravimetry | | Spectral Measurement[b] | | SEM |
|---|---|---|---|---|---|
| | porosity (%) | thickness (nm) | porosity (%) | thickness (nm) | thickness (nm) |
| Single-layer 1 | 81 ± 1 | 2540 ± 35 | 85 ± 4 | 2890 ± 150 | 2572 ± 410 |
| Single-layer 2 | 64 ± 5 | 4435 ± 260 | 66 ± 4 | 5376 ± 160 | 5461 ± 210 |
| double-layer: | | | | | |
| layer 1 (top) | | | 88 ± 4 | 3012 ± 190 | 2940 ± 180 |
| layer 2 (bottom) | | | 63 ± 2 | 5306 ± 140 | 5640 ± 120 |
| combination | 71 ± 1[c] | 7165 ± 450[c] | 72 ± 2 | 8307 ± 300 | 8677 ± 120 |

[a]Porosities and thicknesses of porous Si single- and double-layers as determined by gravimetry, by spectral measurement, and by SEM. "Single-layer 1" was etched at 500 mA/cm$^2$ for 11 s, "single-layer 2" at 167 mA/cm$^2$ for 55 s, and "double-layer" at 500 mA/cm$^2$ for 11 s followed by 167 mA/cm$^2$ for 55 s. All samples have been thermally oxidized in air at 600° C.
[b]For the spectral measurement, calculation of porosity and thickness of "single-layer 1," "single-layer 2," and the top ("layer 1") and bottom ("layer 2") layers of "double-layer" is based on application of the Bruggeman approximation to the values of optical thickness (2 nL) obtained from FFT of the reflectivity spectra of samples immersed in various liquids, as described in the text. Porosity and thickness of "layer 1" in the porous silicon double layers is calculated using a value of EOT determined from the difference in EOT between "combination" (layer 3 in FIG. 1) and "layer 2."
[c]Gravimetric measurements do not distinguish between the two layers of the porous Si double-layers, and provide an average value of porosity and thickness of both layers.

Thickness and porosity of the layers were also determined by optical measurements. The Bruggeman theory, one of a number of effective medium approximations, has been shown to predict the porosity of porous Si in reasonable agreement with gravimetric determinations. In this technique, the porous Si white-light reflection spectrum is measured with the film held in air and in the series of solvents ethanol, acetone, and hexane, having refractive indices 1.360, 1.357, and 1.375, respectively. The difference between the spectra can be attributed to the changes in optical thickness as the medium in the pores changes, with the assumption that all the void spaces in the film are filled equally (i.e., no remaining air bubbles). The value of the product 2 nL, where n and L are the refractive index and the thickness of the film, respectively, are obtained from the reflectivity spectra. For the Bruggeman calculation, only the product nL is used. Data obtained from a given sample in air and in the three liquids is then fit to the two-component Bruggeman approximation, yielding an over-determined solution for both the porosity and the thickness of the sample. The value of refractive index for oxidized porous Si used in the Bruggeman fit that provided the most self-consistent results was 2.1.

The calculated porosities of the porous Si single-layers (Table 1) agree with the results obtained by gravimetry. However, the film thickness values obtained from the Bruggeman calculations and the SEM measurements deviate somewhat from the gravimetric results. This can be explained since the gravimetric measurements do not account for the increase in mass and in volume that occurs etched for 11 s at 500 mA/cm$^2$, followed by 55 s at 167 mA/cm$^2$. "Fit" shows a least-squares fit of the double-layer spectrum to a two-layer interference model (eq. 2), as explained below. The peaks from the fit matching the spectral peaks are indicated with the vertical dashed lines. All spectra were obtained from a spot ~1 mm in diameter on the porous Si film. Spectra of samples were measured in air and are not corrected for instrumental spectral response.

The spectra, obtained using a spectrometer and a white light (tungsten) illumination source in a 90° backscatter configuration, display a series of interference fringes. These fringe patterns result from Fabry-Pérot interference of light reflected from the various interfaces present in the structures. The fringe maxima are described by the Fabry-Pérot relationship given in eq. 1

$$m\lambda = 2nL \quad (1)$$

where m is an integer, L is the thickness of the porous Si layer, n is the average refractive index, and λ is the wavelength of incident light. The factor of 2 derives from the 90° backscatter configuration of the illumination source and detector. The term 2 nL is thus the optical path, referred to as the effective optical thickness (EOT) in this application. The pore dimensions in these structures are too small to effectively scatter light, and each porous layer is treated as a single medium with a single value for refractive index.

As expected from the relationship of eq. 1, the series of Fabry-Pérot fringes observed in the "single-layer 1" and the "single-layer 2" samples are spaced evenly in frequency (FIG. 2). A linear least-squares fit of the wavelength of the peak maxima to eq. 1 yields directly the 2 nL values for "single-layer 1" and "single-layer 2". See, Table 2. The double-layer film displays a more complex fringe pattern that cannot be fit to eq. 1. The spectrum arises from interference in all three layers represented in FIG. 1, and can be fit to a double layer interference model. Ignoring multiple reflections, the reflectance R of light from a double layer is given by:

$$R=(\rho_a^2+\rho_b^2+\rho_c^2)+2\rho_a\rho_b\cos(2\delta_1)+2\rho_b\rho_c\cos(2\delta_2)+2\rho_a\rho_c\cos[2(\delta_1+\delta_2)] \quad (2)$$

where $\delta_i$ represents the phase relationship of layer i:

$$\delta_i = \frac{2\pi n_i L_i}{\lambda} \quad (3)$$

Here $n_i$ represents the refractive index of layer i with thickness $L_i$. The terms $\rho_a$, $\rho_b$, and $\rho_c$ in eq. 2 represent the index contrast at each of the interfaces a, b, or c (see FIG. 1):

$$\rho_a = \frac{n_{air}-n_1}{n_{air}+n_1}, \rho_b = \frac{n_1-n_2}{n_1+n_2}, \rho_c = \frac{n_2-n_{Si}}{n_2+n_{Si}} \quad (4)$$

Where $n_{air}$, $n_1$, $n_2$, and $n_{Si}$ represent the refractive index of air (or of the solution), layer 1, layer 2, and bulk Si, respectively. The quantities $n_1$ and $n_2$ represent the total refractive index of the layer and everything it contains (silicon, $SiO_2$, solution, air, biomolecule, etc.). A least-squares fit of the reflectivity spectrum of the double layer to eq. 2 is shown in FIG. 2. The spectra shown in FIG. 2 are not corrected for the spectral response of the lamp or spectrometer, and the values $\rho_a$, $\rho_b$, and $\rho_c$ cannot be accurately evaluated from such data. Thus the absolute intensity of the spectrum is not fit by the model. However, the phase relationship $\delta_i$ can be reliably extracted, yielding values of 2 nL for layer 1 and for layer 2 of 6200 nm and 13,800 nm, respectively, as seen in Table 2. These values somewhat under-estimate the single-layer values determined from eq. 1 discussed above. Although the models used to fit the data are quite simplified, they provide a consistent picture of the optical properties of these structures.

TABLE 2

Comparison of methods used to evaluate EOT (2 nL) from the reflectivity spectrum: Fabry-Pérot interference calculation vs FFT.[a]

| Porous Si Layer | Fit to Interference Equations (nm)[b] | FFT (nm) |
| --- | --- | --- |
| single-layer 1 | 7220 | 6950 |
| single-layer 2 | 14,400 | 14,400 |
| double-layer: | | |
| layer 1 (top) | 6200 | 6250 |
| layer 2 (bottom) | 13,800 | 13,900 |
| combination | 19,800 | 20,100 |

[a]Thermally oxidized porous Si layers as prepared in Table 1.
[b]"Single-layer 1" and "single-layer 2" calculated from least squares fit to eq. 1. "Double-layer" calculated from least-squares fit to eq. 2.

4. Fast Fourier Transform (FFT) of Reflectance Spectra

A FFT of the spectrum provides a computationally simple and reliable technique for extracting the optical parameters. More complex models can also be used, such as models incorporating the frequency dispersion of refractive index, the effect of multiple reflections, and the instrumental response function. Such models provide a more rigorous description of the optical properties of the porous Si films. However, the FFT is a faster and more convenient method of extracting the optical parameters. The FFT can provide more reliable data for complicated optical structures, in particular when the optical constants are changing due to analyte admission into the pores. For biosensing, the relative change in these optical constants is the important parameter.

Figure 3:
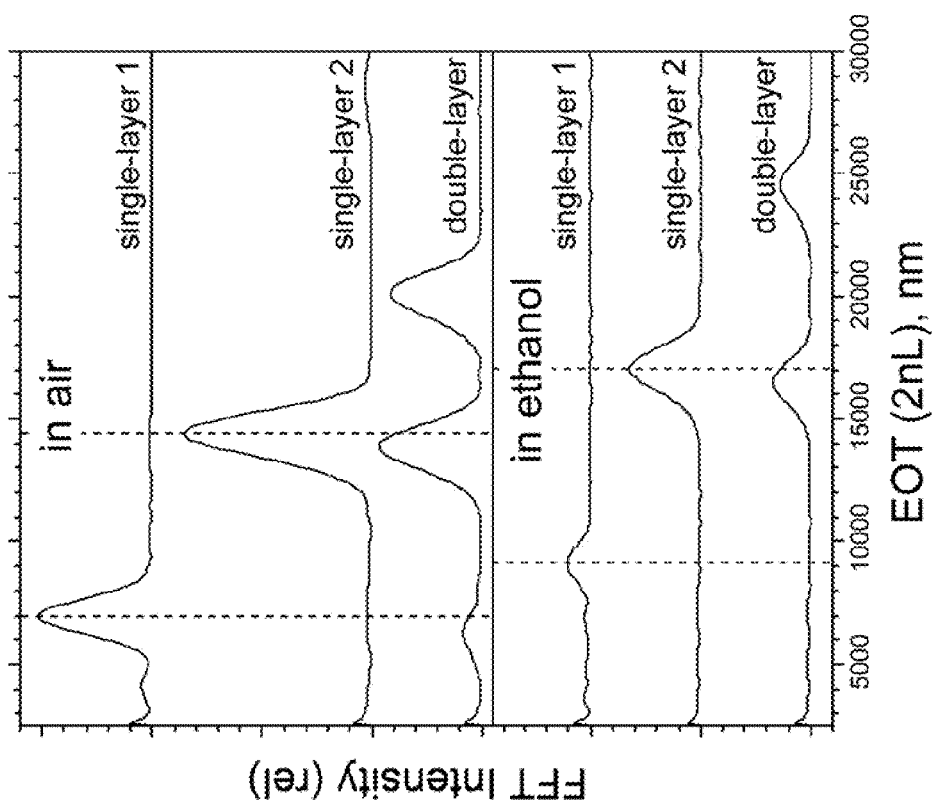
FIG. 3 shows Fourier transforms of the optical interference spectra of FIG. 2.

The Fourier transforms of the optical interference spectra of FIG. 2 are presented in FIG. 3. The complex interference pattern for the double-layer is deconvoluted into its three components (layer 1, layer 2, and layer 1+layer 2) by the Fourier transform. Peaks in the "in ethanol" spectra all display lower intensity relative to the corresponding "in air" spectra due to the decrease in refractive index contrast that occurs when the pores fill with liquid. All spectra were obtained from a spot ~1 mm in diameter, and are offset along the y-axis for clarity.

The value of 2 nL can be obtained directly as the position of the peak in the FFT. Thus the "single-layer 1" film in air displays a spectral interference pattern (FIG. 2) whose FFT yields a peak at 6950 nm (FIG. 3 and Table 2). As mentioned above, the position of this peak in the FFT is equal to the value 2 nL from eq. 1. Similarly, the "single-layer 2" film displays a spectral interference pattern whose FFT yields a peak at 14,400 nm. If more than one layer exists in the film, the FFT yields values of 2 nL for the separate layers as distinct peaks. Thus the ITT of the interference spectrum for the double-layer (FIG. 2, "double-layer") displays 3 peaks (FIG. 3, "double-layer") at 6250, 13,900, and 20,100 nm, corresponding to the values of 2 nL for layers 1, 2, and 3, respectively, as depicted in FIG. 1.

The sum of the values of 2 nL for layer 1 and 2 is predicted by eq. 2 to be equal to the value of 2 nL for layer 3, and there is agreement within the error of the measurement (20,150 nm vs 20,100 nm, respectively). As with the least-squares fits of the spectra to eqs. 1 and 2, the FFT analysis yields a 2 nL value for each individual layer of the double-layer that is smaller than the value obtained from the corresponding single-layer, consistent with the SEM measurements (Table 1).

The information contained in both the intensity and in the position of the peaks in the Fourier transform can be related to the optical constants presented in the double-layer interference model of eq. 2. As discussed above, the position of a peak in the FFT is equal to the EOT, or 2 nL of a porous Si layer. It is related to the phase relationship of eq. 3 by:

$$EOT_i = 2n_iL_i = \frac{\lambda\delta_i}{\pi} \quad (5)$$

Eq. 2 represents a sum of 3 cosine terms corresponding to the 3 optical layers represented in FIG. 1. The frequency of each of the cosine terms is thus related to the EOT of one of the layers. The amplitude of each cosine term is related to the amplitude of light reflected at the interfaces, and therefore related to the index contrast at each pair of interfaces that defines the relevant layer, as given by eq. 4. The amplitude of a peak in the FFT spectrum is proportional to this index contrast:

$$A_1=k\rho_a\rho_b, A_2=k\rho_b\rho_c, A_3=k\rho_a\rho_c \quad (6)$$

where $A_1$, $A_2$ and $A_3$ are the amplitudes of the FFT peaks corresponding to layer 1, 2, and 3 of FIG. 1, respectively, $\rho_a$, $\rho_b$, and $\rho_c$ are as defined above for eq. 4, and k is a proportionality constant. The relationship of FFT peak amplitude to index contrast is only strictly valid if the spectrum from which the FFT derives is an absolute reflectivity spectrum (corrected for instrument response). In that case, k=2. In the present application, uncorrected intensity-wavelength spectra are used (see below). The FFT contains the necessary information to determine the optical constants of the films relevant for sensing; in particular the refractive index of the film. The position of a given peak measures the refractive index of the layer, and the amplitude measures the refractive index contrast of the layer, relative to its neighboring layers. The relationships of eqs. 5 and 6 provide the key to extracting a reference channel from the double-layer interferometers described in this application.

5. Changes in the Optical Parameters Due to Infiltration of Molecules

Infiltration of a liquid into the porous structures leads to predictable changes in both the position and in the intensity of the peaks in the FFT spectrum. The intensity changes correspond to changes in the relative reflectivity of the various interfaces in the structure. As seen in FIG. 3, peaks in the FFT of spectra from the "in ethanol" samples all display lower intensity relative to the corresponding "in air" peaks. This is attributed to the decrease in refractive index contrast that occurs when the pores fill with liquid, as predicted by the relationships of eqs 4 and 6. Additionally, the peak corresponding to layer 1 of the double-layer, already weak in the "in air" spectrum, disappears completely in the "in ethanol" spectrum, indicating an almost complete disappearance of index contrast in that layer relative to the surrounding layers. The reduction in index contrast when a single-layer or double-layer film is immersed in liquid is also observed in the reflectivity spectrum, manifested as a decrease in fidelity of the Fabry-Pérot fringes.

The decrease in intensity of the FFT peaks that occurs when the sample is immersed in liquid is most noticeable for samples that have been extensively oxidized, where the refractive index of the solid component of the porous film is closer to pure $SiO_2$ (n=1.5) than to Si (n=3.8). Ozone-oxidation is milder, producing less $SiO_2$ in the film. For a given porosity, ozone-oxidized films have a larger refractive index than thermally oxidized films, and the peak corresponding to "layer 1" is more discernable in the FFT when such samples are immersed in liquids. However, the ozone-oxidized films were found to be insufficiently stable in the aqueous solutions, and so the thermally oxidized films are preferred for introduction of molecules via an aqueous solution.

Shifts in the position of the peaks in the FFT spectrum indicate a change in average refractive index (EOT or 2 nL) of the film. Infiltration of ethanol into the pores leads to an increase in the value of EOT for either the single- or the double-layer films. The "single-layer 1" film displays a spectrum with a peak in the Fourier transform at 6950 nm in air, increasing to 9080 nm in ethanol. Similarly, the FFT peak from the "single-layer 2" film shifts from 14,400 nm to 17,000 nm when the film is placed in the liquid.

The peaks in the FFT spectrum of the double-layer also shift upon infiltration of ethanol, in line with the single-layer results. As mentioned above, the peak corresponding to layer 1 of the double-layer structure often become too weak to observe upon immersion in ethanol due to the loss in index contrast, but the peaks corresponding to layer 2 and to the combination of both layer 1 and layer 2 (layer 3 of FIG. 1) are observable (FIG. 3). Since the combination represents a sum of layers 1 and 2 (eq. 2), the position of the peak corresponding to layer 1 can be calculated as the quantity ($EOT_3$–$EOT_2$). Using this relationship, the 2 nL value for layer 1 shifts by 1780 nm, from 6250 nm in air to 8030 nm in ethanol, and for layer 2 the shift is 2600 nm, from 13,900 nm to 16,500 nm.

6. Sensing of Bovine Serum Albumin and Sucrose in Double Layers

The penetration of biomolecules into a porous Si Fabry-Pérot layer leads to an increase in EOT resulting from partial replacement of aqueous buffer by molecules with a larger index of refraction. Bovine serum albumin (BSA) and sucrose were used to test the ability of the porous Si double-layer to discriminate biomolecules of different sizes. BSA is a heart-shaped protein with dimensions roughly of the order of 3×8×8 nm (at pH 4) and a molecular weight of 68 kDa. Sucrose is a small molecule with dimensions less than 2×2×2 nm, and a molecular weight of 342 g/mol. Because of the difference in pore dimensions between the two layers of the double-layer, both molecules are expected to be admitted into layer 1 and only sucrose is expected to enter into layer 2.

Aqueous buffer solutions of the test molecules were introduced to the porous Si films using a transparent flow-cell such that real-time reflectivity spectra could be obtained. The flow-cell was flushed with either pure pH 4 buffer or pure pH 7 buffer followed by pure pH 4 buffer in between samples. The purpose of the pH 7 rinse is to more efficiently remove the BSA molecule from the oxidized porous Si surface by changing the net charge on the molecule. The isoelectric point of BSA is 4.8, so at pH 4 it has a net positive charge while oxidized porous Si is negative, leading to strong non-specific binding. At pH 7 both BSA and oxidized porous Si are negatively charged, and electrostatic forces aid in expulsion of the protein from the pores.

Protein adsorption to silica is an extremely complex process that depends on pH, temperature, ionic strength, and solvent properties. Others have shown attachment of poly-ethylene glycol) or large biomolecules to the inner pore surfaces minimizes non-specific adsorption to porous Si.

In the experiments, the surfactant Triton X-100 was added to the solutions in order to enhance diffusion of BSA out of the pores of thermally oxidized porous Si. It was found that even the addition of detergent could not displace all of the BSA from the surface, and the initial introduction of BSA to the porous Si double-layer forms a thin coating that is not removed with subsequent rinsing steps. Thus, all samples in the biomolecule binding studies were pre-treated with BSA solution and then rinsed with pH 7 buffer followed by pH 4 buffer. After this "pre-treatment" which led to a new baseline, both sucrose and BSA were found to readily diffuse in and out of the pores and to provide reproducible binding curves during the flow cell experiments. Sucrose is a neutral molecule, and did not display any such enhanced binding effects with the samples used in the present study.

7. Shifts in FFT Peak Positions (EOT) on Exposure to BSA and Sucrose

The response of the layers can be probed using the FFT methods, as described above. As described above, the interference spectrum of a double-layer film displays a complicated pattern of maxima and minima that corresponds to a combination of the Fabry-Pérot interference spectra from the three layers defined in FIG. 1. Additional layers would provide additional interference spectra. The FFT deconvolutes the spectrum, and can distinguish between the filling of the big pores and the small pores.

Figure 4:
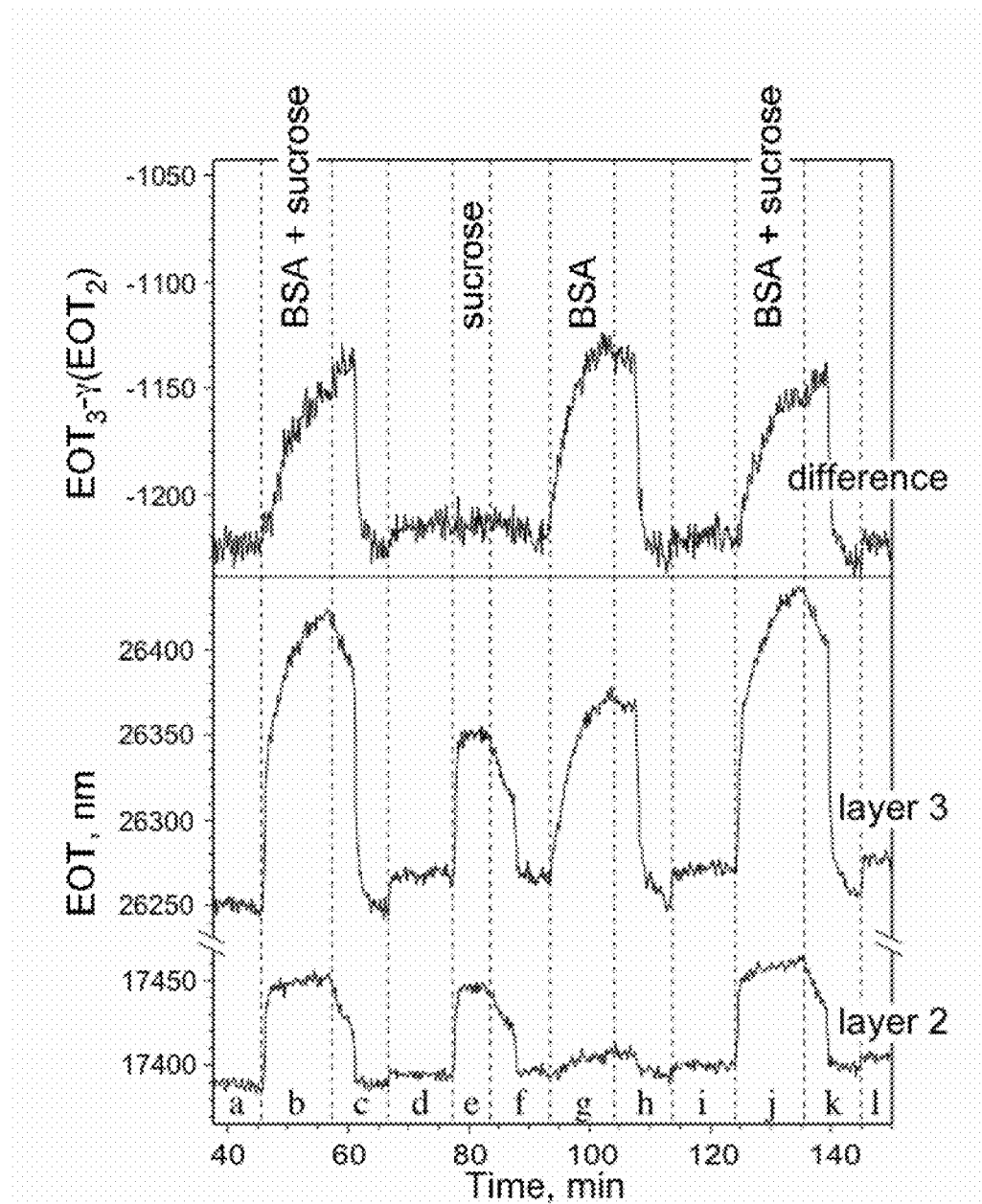
FIG. 4 shows the shift of the two FFT peaks corresponding to layer 2 (the layer with small pores) and layer 3 (the combination of layer 1 and layer 2, see FIG. 1) versus time during a flow cell experiment.

FIG. 4 shows the shift of the two FFT peaks corresponding to layer 2 (the layer with small pores) and layer 3 (the combination of layer 1 and layer 2, see FIG. 1) versus time during a flow cell experiment. For the experiment described by FIG. 4, the sample was successively exposed to a buffer solution containing BSA with excess sucrose, sucrose alone, BSA alone, and then again BSA with sucrose. FIG. 4 shows the effect of introduction of sucrose and bovine serum albumin (BSA), separately and in combination, on the effective optical thickness (EOT, or 2 nL) of layers 2 and 3 of a thermally-oxidized double-layer sensor. EOT for a given layer is measured as the position of the corresponding peak in the FFT spectrum. Layer 2 contains the smaller pores, and does not respond to the larger BSA molecule. Layer 3 represents the combination of layer 1 and 2 (see FIG. 1) and so responds to both BSA and sucrose. The weighted ($\gamma$=1.58) difference of the EOT values from the two films, shown as the top trace, eliminates the effect of sucrose, allowing selective detection of BSA. (a) pH 4 buffer (potassium biphthalate), (b) 1 mg/mL BSA and 59 mg/mL sucrose in pH 4 buffer, (c) pH 4 buffer, followed by pH 7 buffer, (d) pH 4 buffer, (e) 50 mg/mL sucrose in pH 4 buffer, (f) pH 4 buffer, (g) 1 mg/mL BSA in pH 4 buffer, (h) pH 4 buffer, followed by pH 7 buffer, (i) pH 4 buffer, (j) 1 mg/mL BSA and 50 mg/mL sucrose in pH 4 buffer, (k) pH 4 buffer, followed by pH 7 buffer, (l) pH 4 buffer. All data were acquired under a constant peristaltic flow of 0.5 mL/min in a flow cell. The sample had been pre-treated by exposure to BSA at pH 4 followed by a rinse with pure buffer at pH 7.

When the double-layer sample is exposed to a solution containing 1 mg/mL of BSA and 50 mg/mL sucrose, the FFT peaks corresponding to layers 2 and 3 shift to larger values, corresponding to an increase in EOT as the molecules enter the pores (FIG. 4, region b). When only sucrose is added (FIG. 4, region e), the peak assigned to layer 2 increases by the same amount, and the peak assigned to layer 3 increases by approximately half of the BSA+sucrose value. The responses are additive, with layer 3 showing approximately the same response to 1 mg/mL of BSA as it does to 50 mg/mL of sucrose. The greater response that layer 3 displays towards BSA relative to sucrose derives from the increased non-specific binding interaction of the protein.

When only BSA is added (FIG. 4, region g), the peak assigned to layer 2 does not increase at all, indicating that the pores of this layer are not large enough to admit the protein. The peak assigned to layer 3 again only increases by approximately half of the BSA+sucrose value. A final dose containing both BSA and sucrose (FIG. 4, region j) replicates the initial dose. This data indicates that the small molecule sucrose can penetrate both layers, while the large protein BSA only enters the top layer (layer 1).

8. Detection of Biomolecules in Double-Layers by Differential EOT Measurement

The main difference in composition between layer 1 and layer 2 is that layer 1 contains the protein BSA and layer 2, because of its smaller pores, does not. In addition, because they have different porosities, the relative amount of $SiO_2$ and solution are different in each layer. If this latter difference can be accounted for, then a technique to measure the binding of protein in the film is provided. Binding of protein can be measured as the difference in index between layer 1 ($n_1$) and layer 2 ($n_2$). Since the total refractive index of a layer is related to its EOT by eq. 5, the difference can be expressed as:

$$EOT_3 - \gamma EOT_2 = n_1 L_1 + n_2 L_2 (1-\gamma), \quad (7)$$

Here the term $\gamma$ is a weighting factor that accounts for the differences in porosity and thickness between the two layers. It assumes that the index of a layer is proportional to its fractional composition, which is not strictly valid if the Bruggeman effective medium approximation applies. However, for small changes in n as encountered in the present biosensing application it is approximately correct. If $\gamma$=2 and $L_1$=$L_2$, the left side of eq. 7 reduces to $(n_1-n_2)L$, as expected. The quantity $\gamma$ indicates how the relative responses of the two layers scale with each other, and can be determined empirically from the sucrose data by application of eq. 8:

$$\gamma = \frac{EOT_3(\text{sucrose}) - EOT_3(\text{buffer})}{EOT_2(\text{sucrose}) - EOT_2(\text{buffer})} \quad (8)$$

Where $EOT_i(\text{sucrose})$ is the EOT measured for layer i infused with buffer containing sucrose, and $EOT_i(\text{buffer})$ is the EOT measured for layer i infused with buffer only. For the data in FIG. 4, a value of 1.58 was determined for $\gamma$. A plot of the quantity ($EOT3-\gamma EOT2$) then detects BSA only, essentially nulling the response to sucrose (FIG. 4).

Figure 5:
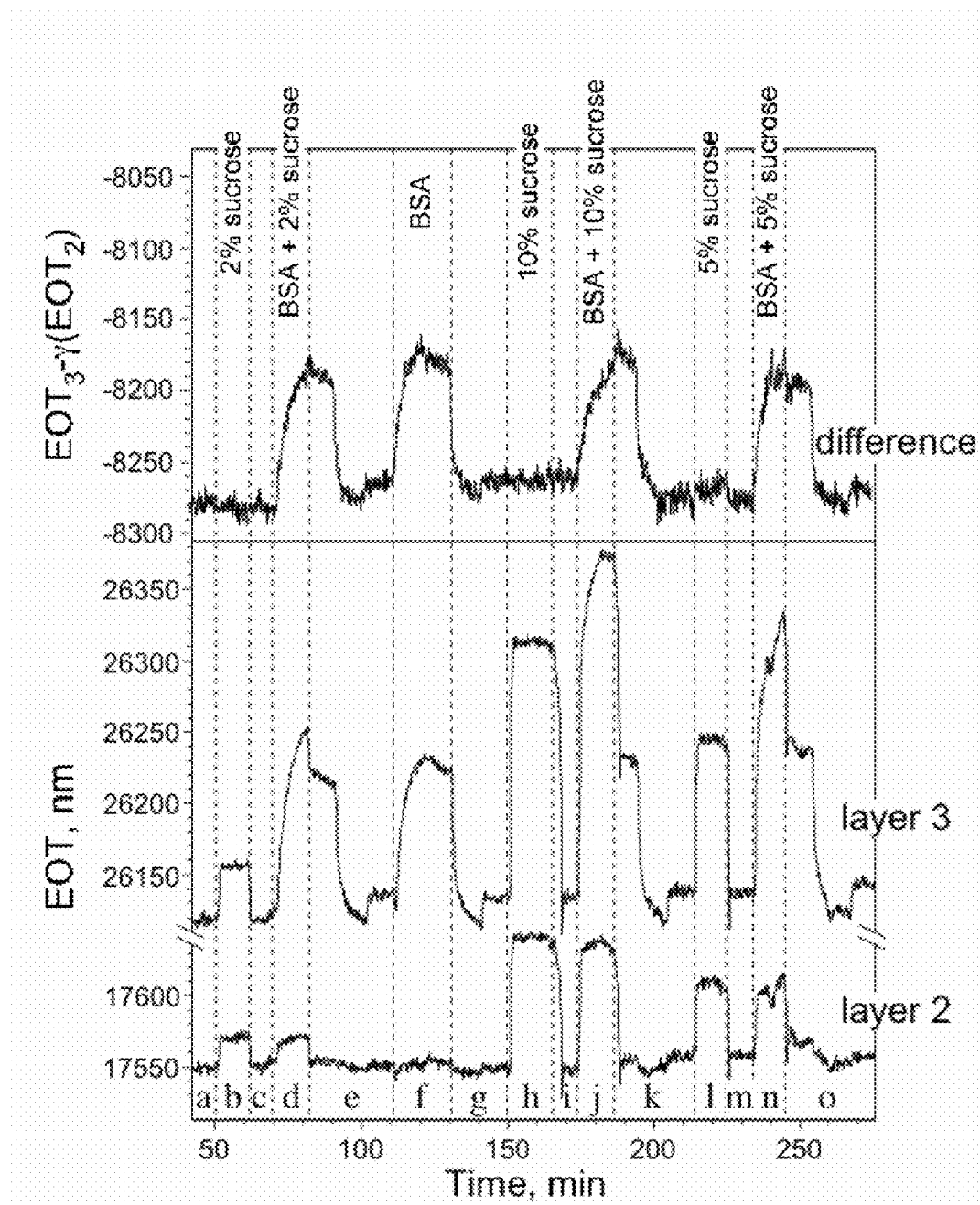
FIG. 5 shows the effect of a changing sample matrix on the differential change in refractive index (EOT) measurement in response to bovine serum alum (BSA) and sucrose.

9. Dependence of Differential EOT Measurement on Concentration of Matrix Interferents The effect of a changing sample matrix on the differential EOT measurement is shown in FIG. 5. Dependence of the EOT values of a thermally-oxidized double layer sensor towards BSA (1 mg/mL) in the presence of changing concentrations of sucrose. The weighted ($\gamma$=1.96) difference of the EOT values from the two films, shown as the top trace, eliminates the effect of sucrose at all concentrations, allowing selective detection of BSA. The effective optical thickness (EOT, or 2 nL) of layers 2 and 3 and the weighted difference of the two values are plotted as in FIG. 5. Layer 2 contains the smaller pores, and does not respond to the larger BSA molecule. Layer 3 represents layer 1 and 2 (see FIG. 1) and so responds to both BSA and to sucrose. (a) pH 4 buffer, (b) 20 mg/mL sucrose in pH 4 buffer, (c) pH 4 buffer, (d) 1 mg/mL BSA and 20 mg/mL sucrose in pH 4 buffer, (e) pH 4 buffer, followed by pH 7 buffer, then by pH 4 buffer, (f) 1 mg/mL BSA in pH 4 buffer, (g) pH 4 buffer, followed by pH 7 buffer, then by pH 4 buffer, (h) 100 mg/mL sucrose in pH 4 buffer, (i) pH 4 buffer (j) 1 mg/mL BSA and 100 mg/mL sucrose in pH 4 buffer, (k) pH 4 buffer, followed by pH 7 buffer, then pH 4 buffer, (l) 50 mg/mL sucrose in pH 4 buffer, (m) pH 4 buffer, (n) 1 mg/mL BSA and 50 mg/mL sucrose in pH 4 buffer, (o) pH 4 buffer, followed by pH 7 buffer, then pH 4 buffer. All data were acquired under a constant peristaltic flow of 0.5 mL/min in a flow cell. Sample had been pre-treated by exposure to BSA at pH 4 followed by a rinse with pure buffer at pH 7.

In this experiment, a constant amount of BSA (1 mg/mL) is tested in the presence of sucrose concentrations varying from 0 to 100 mg/mL. The effective optical thickness (EOT, or 2 nL) of layers 2 and 3 and the weighted difference of the two values are plotted as in FIG. 4. As with the sample of FIG. 4, the pores in layer 2 are too small to admit BSA, and this layer only responds to sucrose. Layer 3, consisting of both the large pore (layer 1) film and the small pore (layer 2) film, responds to both BSA and to sucrose. The weighted difference of the EOT values from the two films, shown as the top trace in FIG. 5, completely eliminates the response from sucrose at all concentrations, allowing selective detection of BSA. For this sample the value of $\gamma$ was determined to be 1.96 (by application of eq. 8).

10. Detection of Biomolecules in Double-Layers by Measuring Shifts in FFT Peak Intensity The amplitude of a peak $A_i$ in the FFT spectrum is related to the reflectivity of the two interfaces bordering layer i by eq. 6. The reflectivity at a given interface is related to the index contrast by eq. 4. When protein infuses into either layer 1 or layer 2, it exerts an effect on the magnitude of $A_i$ for both layers, since they share a common interface. Binding of protein can be measured as the ratio of peak amplitudes $A_1$ to $A_2$. This ratio is related to the index contrast at two of the three interfaces present in the double-layer (eq. 4 and 6) by eq. 9:

$$\frac{A_1}{A_2} = \frac{k\rho_a\rho_b}{k\rho_b\rho_c} = \frac{\rho_a}{\rho_c} \qquad (9)$$

Here, there is no weighting factor to account for differences in porosity and thickness between the two layers as was introduced in eq. 7. In the present case the data deriving from layer 1 is used instead of layer 3. In some instances the amplitude $A_1$ in the FFT spectrum can be too small to measure reliably, especially when using fully oxidized porous Si (where the index contrast of layer 1 is small relative to its neighboring layers). In such cases it is also possible to isolate the response to BSA by plotting the ratio $A_3/A_2$.

Figure 6:
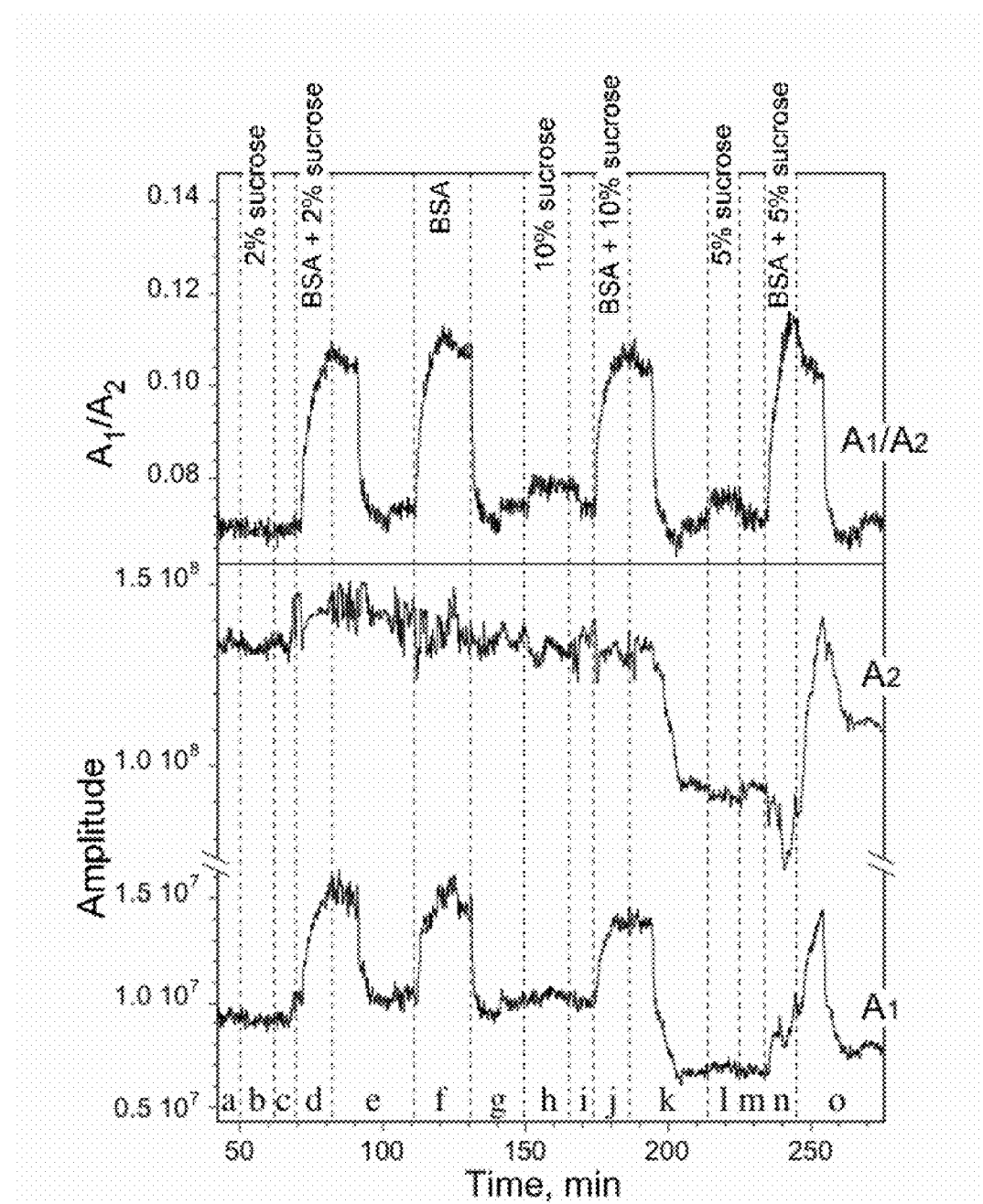
FIG. 6 shows the amplitude of the FFT peaks corresponding to layer 1 and layer 2 of the double-layer ($A_1$ and $A_2$), and the ratio of $A_1$ to $A_2$ for the data of FIG. 5.

The amplitude of the FFT peaks corresponding to layer 1 and layer 2 of the double-layer ($A_1$ and $A_2$), and the ratio of $A_1$ to $A_2$ are presented in FIG. 6. The raw data sets from FIG. 5 were used. FIG. 6 shows the dependence of the amplitude of the FFT peaks from the double layer sensor towards BSA (1 mg/mL) in the presence of changing concentrations of sucrose, as in FIG. 5. $A_1$ and $A_2$ represent the integrated areas of the FFT peaks corresponding to layer 1 and layer 2 ($A_1$ and $A_2$ of eq. 6) respectively. The ratio of $A_1$ to $A_2$ is shown in the top trace. The ratio eliminates the effect of sucrose at all concentrations, allowing selective detection of BSA. The absolute scales for $A_1$ and $A_2$ differ. The labels (a) through (o) are the same as in FIG. 5.

As can be seen, the plots of $A_1$ and $A_2$ vs time are very noisy. The noise in the measurement relates to fluctuations in lamp intensity, bubbles in the flow cell, cell temperature, and other undetermined experimental variables during the course of the measurement. The measurement of EOT (FFT peak position) is less sensitive to such variations. However, the errors apparent in the plots of $A_1$ and $A_2$ are correlated, and they are effectively eliminated in the ratio of $A_1$ to $A_2$, as shown in FIG. 6. The quantity $A_2$ represents the product of the index contrast at both the bulk Si/layer 2 interface and the layer 1/layer 2 interface. It does not change significantly with either a large dose of sucrose or with BSA. The quantity $A_1$ represents the product of the index contrast at both the layer 1/layer 2 interface and the bulk solution/layer 2 interface, and it tracks the admission of protein into layer 1. Although $A_2$ appears to contain no information, it tracks lamp fluctuations, bubbles, and other sources of experimental error that also appear in $A_1$. In particular, note point k in the traces of FIG. 6, the stage at which the largest dose of sucrose/BSA is removed; the relative reflectivity of the interfaces changes dramatically, but the ratio $A_1/A_2$ successfully nulls the effect.

11. Experimental Procedures

All reagents were used as received. Potassium phosphate pH 7 buffer was obtained from Fisher, Inc. as a 0.05 M potassium phosphate Certified Buffer Solution (Cat. No. SB108-20). The potassium biphthalate pH 4 buffer was obtained from Fisher, Inc. as a 0.05 M potassium biphthalate Certified Buffer Solution (Cat. No. SB98-500). Bovine Serum Albumin (BSA), lyophilized powder, 1× crystallized, >97% purity, was obtained from Sigma-Aldrich (Cat. No. A 4378). Sucrose was obtained from EM Science (Cat. No. SX 1075-1). Aqueous HF (48%) and ethanol (99.9%) were supplied by Fisher Scientific and AAper, respectively. Porous Si samples were prepared from single-crystalline highly-doped p-type Si (0.0008-0.0012 Ω-cm resistivity, <100> oriented, B-doped, from Siltronix Corp.)

Porous Si samples were prepared by anodization of the degenerately doped p-type Si wafers in ethanolic HF solution (3:1 v/v 48% aqueous HF:ethanol) in a two-electrode configuration using a platinum mesh counter-electrode. Si wafers with an exposed area of 1.2 cm$^2$ were contacted on the back side with a strip of aluminium foil and mounted in a Teflon etching cell. Galvanostatic anodization was performed in the dark. Single-layers were etched by applying 500 mA/cm$^2$ for 11 s ("single-layer 1") or 167 mA/cm$^2$ for 55 s ("single-layer 2"). Double-layer samples were prepared by application of 500 mA/cm$^2$ for 11 s followed immediately by application of 167 mA/cm$^2$ for 55 s. After etching, the samples were rinsed thoroughly with ethanol and then dried under a stream of nitrogen.

Scanning electron microscopy (SEM) images were obtained with a Cambridge EM-360 electron microscope using an accelerating voltage of 20 keV. In order to avoid sample charging anomalies, the porous Si samples were sputter-coated with a thin layer of gold (20 nm) prior to the SEM analysis.

Interferometric reflectance spectra of porous Si were collected by using an Ocean Optics CCD S-2000 spectrometer fitted with a microscope objective lens coupled to a bifurcated fiber optic cable. A tungsten light source was focused onto the center of a porous Si surface with a spot size of approximately 1-2 mm$^2$. Reflectivity data were recorded with a CCD detector in the wavelength range of 400-1000 nm, with a spectral acquisition time of 100 ms. Typically 10 spectral scans (1 s total integration time) were averaged before FFT processing. Both the illumination of the surface and the detection of the reflected light were performed along an axis coincident with the surface normal.

Porous Si samples were thermally oxidized by heat treatment in a tube furnace (Fisher Blue M). The samples were heated at 600° C. for 1 h in ambient air, then allowed to cool to room temperature.

Three porous Si samples were weighed on a laboratory balance with a resolution of 10 μg before ($m_1$) and after etching at mA/cm$^2$, respectively. Each sample was thermally oxidized and weighed again ($m_2$). The oxidized porous Si layer was then dissolved in 48% aqueous HF:ethanol (3:1, v:v), and the wafer remaining was weighed ($m_3$). The porosity P was calculated using the following equation:[24]

$$P = \frac{m_1 - m_2}{m_1 - m_3}$$

The thickness W of the porous Si layer was determined by applying the equation:

$$W = \frac{m_1 - m_2}{Sd}$$

where S is the wafer area exposed to HF during the electrochemical etching and d is the density of bulk Si.

Biomolecule penetration experiments were carried out in a custom-made flow cell. Briefly, the flow cell was constructed of plexiglass and connected via an outlet and inlet to a peristaltic pump. The light beam was focused on the surface of the sample through the plexiglas cover and interference spectra were recorded.

The wavelength axis of the spectrum from the Ocean Optics spectrometer was calibrated using a least-squares fit of five spectral lines observed from a neon lamp, at 585.3, 614.3, 640.2, 703.2, and 811.5 nm. The data spacing is approximately 0.4 nm. The x-axis was inverted and a linear interpolation was applied such that the data were spaced evenly in units of $nm^{-1}$. A Hanning window was applied to the spectrum, it was redimensioned to 4096 data points and the zero padded to the power of two. A discrete Fourier transform using a multidimensional fast prime factor decomposition algorithm from the Wavemetrics, inc IGOR program library (FFT) was applied.

Protein A and Rabbit Immunoglobulin

Peak Amplitude Shift Experimental Results

12. Fabrication of Two Layer Biosensor

The example biosensors for this experiment were generally consistent with FIG. 1 and the procedures outlined above. In this case, the biosensor was prepared by electrochemically etching single-crystal silicon (p-type, ca. 1 mΩ-cm, 100 orientation) in aqueous ethanolic HF solution (3:1 v/v 48% aqueous HF:ethanol), using a short period of high applied current (250 mA/$cm^2$ for 23 s) followed by a longer period at low current (83 mA/$cm^2$ for 115 s). The current waveform produces a high porosity, low refractive index layer on top of a lower porosity, higher refractive index layer (see, FIG. 1).

13. Results Summary

Figure 7:
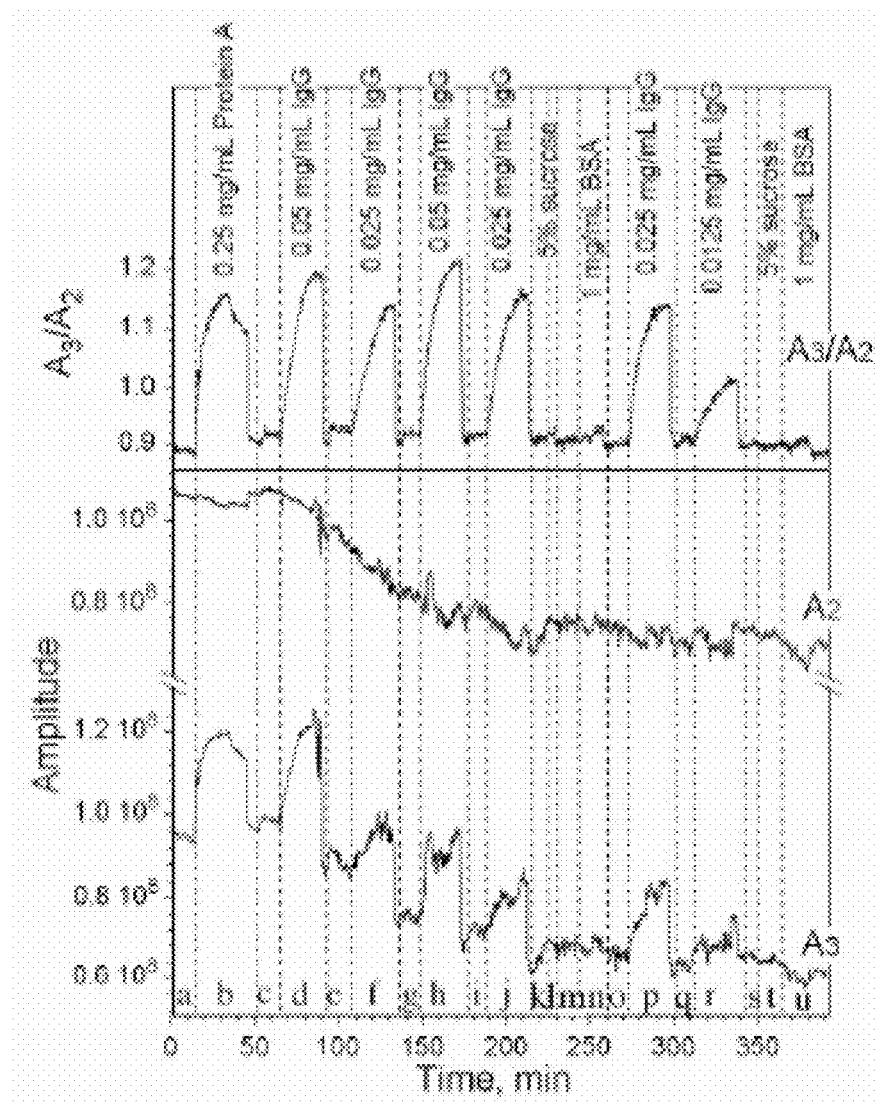
FIG. 7 shows the response of another example experimental embodiment biosensor consistent with FIG. 1 responsive to Protein A and rabbit IgG.

Spectra were taken to determine the response of the biosensor to Protein A (FIG. 7, region b) suggests that exposure to high concentrations of Protein A (0.25 mg/mL) leads to either a closely packed or multilayer adsorption, with the number of adsorbed Protein A molecules being greatly reduced upon rinsing with buffers (end of region b). In FIG. 7, the ratio of $A_3$ to $A_2$ is shown in the top trace. The ratio eliminates baseline drift and significantly reduces noise in the measurement of rabbit IgG binding. BSA does not interact with the surface, while refractive index changes due to penetration of small molecules such as sucrose and buffer into both porous silicon layers are cancelled by the ratio procedure, so none of these species are detected. FIG. 7 shows the response of: a) Phosphate Buffered Saline Solution (PBS) buffer; b) 0.25 mg/ml Protein A in PBS, followed by PBS, then by 0.1 M acetic acid; c) PBS; d) 0.05 mg/ml rabbit IgG, followed by PBS, then 0.1 M acetic acid; e) PBS; f) 0.025 mg/ml rabbit IgG, followed by PBS, then 0.1 M acetic acid; g) PBS; h) 0.05 mg/ml rabbit IgG, followed by PBS, then 0.1 M acetic acid; i) PBS; j) 0.025 mg/ml rabbit IgG, followed by PBS, then 0.1 M acetic acid; k) PBS; l) 50 mg/ml sucrose in PBS; m) PBS; n) 1 mg/ml BSA in PBS, followed by PBS, then 0.1 M acetic acid; o) PBS; p) 0.025 mg/ml rabbit IgG, followed by PBS, then 0.1 M acetic acid; q) PBS; r) 0.0125 mg/ml rabbit IgG, followed by PBS, then 0.1 M acetic acid; s) PBS; t) 50 mg/ml sucrose in PBS, followed by PBS; u) 1 mg/ml BSA in PBS, followed by PBS, then 0.1 M acetic acid and PBS.

The response of the protein A-modified sensor to IgG (ratio change ca. 0.27 for 0.05 mg/mL) is approximately ten times greater than the change observed for strongly-adsorbed Protein A (ca. 0.029). Part of this difference is due to the differences in molecular weight (Protein A: 42 kDa, Rabbit IgG ca. 150 kDa), which can account for ~3.6-fold difference in response. The additional difference may be due to Protein A binding two IgG molecules under these conditions as has been reported for some solution studies or to differences in the refractive index of IgG relative to Protein A. The sensor response here is proportional to a change in the interfacial refractive index contrast rather than just a change in magnitude of the index.

The double-layer biosensor provides a quantitative measurement of equilibrium binding constants. The thermodynamic equilibrium binding constant can be obtained from the $A_3/A_2$ signal at equilibrium for various analyte concentrations by application of a Langmuir fit to the binding isotherm. A fit of the average values of three trials yields a calculated equilibrium dissociation constant $K_n$ of $3 \times 10_{-7}$ mol/L for rabbit IgG binding to protein A, consistent with the published values. The results demonstrate that you can use a change in intensity of the peaks to correct for background.

Example Extensions of Experiments and Preferred Embodiments

The approach should also be amenable to other label-free transduction modalities that utilize refractive index changes, such as surface plasmon resonance or microcavity resonance. The built-in reference channel and Fourier method of analysis provides a general means to compensate for changes in sample matrix, non-specific binding, temperature, and other experimental variables.

An advantage of the interferometric biosensor optical structures of the invention compared to other optical transduction methods is that the sensitivity of the measurement can be improved. Additionally, compared to other optical transduction methods, the equipment needed to monitor binding events can be simplified. The interferometric biosensor of preferred embodiments provides the basis to incorporating sophisticated detection functions, such as correction for drifts due to thermal fluctuation, changes in sample composition, or degradation of the sample matrix.

While various embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the following claims.

The invention claimed is:

1. A method for biosensing, the method comprising:
exposing a biological analyte to a multi-layer microporous thin film structure that has a top layer with larger pores than a second layer, the pores being sized to produce multiple superimposed interference patterns that can be resolved in the reflectivity spectrum;
exposing the multi-layer micro-porous thin film structure to light to produce a reflectivity spectrum;
sensing the reflectivity spectrum to obtain reflectivity data;
extracting optical parameters from the reflectivity data;
determining, from the optical parameters, whether at least one biomolecule of interest is present in said biological analyte, wherein said extracting comprises fitting the interference spectrum to a double layer interference model, and wherein the double layer interference model comprises computing optical interference spectra from a model of reflectance R of light given by:

$$R=(\rho_a^2+\rho_b^2+\rho_c^2)+2\rho_a\rho_b \cos(2\delta_1)+2\rho_b\rho_c \cos(2\delta_2)+2\rho_a\rho_c \cos[2(\delta_1+\delta_2)] \quad \text{(Eq 2)}$$

where $\delta_i$ represents the phase relationship of layer i:

$$\delta_i = \frac{N\pi n_i L_i}{\lambda}$$

$n_i$ represents the refractive index of layer i with thickness $L_i$, N is a constant related to a configuration of a light source and detector respectively used in said steps of sensing and detecting, the terms $\rho_a$, $\rho_b$, and $\rho_c$ in eq. 2 represent the index contrast at each of the interfaces a, b, or c (top surface a, transition from top layer to second layer, and bottom of second layer):

$$\rho_a = \frac{n_{air}-n_1}{n_{air}+n_1},\ \rho_b = \frac{n_1-n_2}{n_1+n_2},\ \rho_c = \frac{n_2-n_{Si}}{n_2+n_{Si}}$$

where $n_{air}$, $n_1$, $n_2$, and $n_{Si}$ represent the refractive index of air (or of a solution), layer 1, layer 2, and material used to form the thin film, respectively, the quantities $n_1$ and $n_2$ represent the total refractive index of the layer and everything it contains.

2. The method of claim 1, wherein the phase relationship $\delta_i$ is extracted.

3. The method of claim 1, further comprising computing a fast Fourier transform of the optical interference spectra to deconvolve its interference pattern into components consisting of a top layer component, a second layer component and a top plus second layer component.

4. The method of claim 1, wherein the multi-layer microporous thin film consists of the top layer, the second layer and bulk silicon.

5. The method of claim 4, wherein the the top layer and second layer are thermally oxidized.

* * * * *